(12) United States Patent
Johnson et al.

(10) Patent No.: US 12,280,225 B2
(45) Date of Patent: Apr. 22, 2025

(54) CATHETER WITH THREADING FLASH CONFIRMATION

(71) Applicant: ICU Medical, Inc., Plymouth, MN (US)

(72) Inventors: Daniel Casey Johnson, Minneapolis, MN (US); Eric Jason Krause, Big Lake, MN (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/757,264

(22) PCT Filed: Oct. 19, 2018

(86) PCT No.: PCT/US2018/056711
§ 371 (c)(1),
(2) Date: Apr. 17, 2020

(87) PCT Pub. No.: WO2019/079719
PCT Pub. Date: Apr. 25, 2019

(65) Prior Publication Data
US 2021/0187252 A1 Jun. 24, 2021

Related U.S. Application Data

(60) Provisional application No. 62/575,045, filed on Oct. 20, 2017.

(51) Int. Cl.
*A61M 25/06* (2006.01)
*A61B 5/15* (2006.01)
(Continued)

(52) U.S. Cl.
CPC ... *A61M 25/0693* (2013.01); *A61B 5/150381* (2013.01); *A61B 5/1535* (2013.01);
(Continued)

(58) Field of Classification Search
CPC ........ A61M 2025/004; A61M 25/0023; A61M 2025/006; A61M 25/0068;
(Continued)

(56) References Cited

U.S. PATENT DOCUMENTS 4,317,445 A 3/1982 Robinson
4,666,438 A * 5/1987 Raulerson ............. A61M 5/158
604/272

(Continued)

FOREIGN PATENT DOCUMENTS

JP 2000116791 A * 4/2000 ........ A61M 25/0606

OTHER PUBLICATIONS

PCT International Search Report and Written Opinion for International Application No. PCT/US2018/056711 mailed Feb. 1, 2019, 12 pages.

*Primary Examiner* — William R Carpenter
*Assistant Examiner* — Robert F Allen
(74) *Attorney, Agent, or Firm* — Husch Blackwell LLC

(57) ABSTRACT

An intravenous catheter assembly configured to provide two-stage visual indication during catheter insertion into a vein of a patient. The catheter insertion assembly including an insertion needle and a catheter coaxially positioned over the insertion needle to define an annular space between a radial wall of the insertion needle in a flexible wall of the catheter divided into a first axial chamber and a second axial chamber by a formed region of the flexible wall having a diameter configured to inhibit flow between the first axial chamber and the second axial chamber, thereby enabling blood to flow into the first axial chamber when the insertion needle and catheter are in an initial position, and enabling blood to flow into the second axial chamber when the insertion needle and catheter translate axially relative to one another.

2 Claims, 7 Drawing Sheets

(51) Int. Cl.
  *A61B 5/153* (2006.01)
  *A61M 5/32* (2006.01)
  *A61M 25/00* (2006.01)
  *A61M 25/01* (2006.01)

(52) U.S. Cl.
  CPC ........ *A61M 5/329* (2013.01); *A61M 25/0023* (2013.01); *A61M 25/0606* (2013.01); *A61M 2025/0004* (2013.01); *A61M 2025/006* (2013.01); *A61M 2025/0175* (2013.01); *A61M 2205/583* (2013.01)

(58) Field of Classification Search
  CPC .. A61M 2025/0073; A61M 2025/0175; A61M 25/0606; A61M 25/0693; A61M 2205/583; A61M 25/0028; A61M 25/0032; A61M 5/329; A61M 2025/0004; A61B 5/150381; A61B 5/1535
  See application file for complete search history.

(56) References Cited

U.S. PATENT DOCUMENTS

| | | | | |
|---|---|---|---|---|
| 5,078,687 A * | 1/1992 | Egolf | ............... | A61M 25/0606 604/164.02 |
| 5,126,090 A * | 6/1992 | Egolf | ............... | A61M 25/0009 264/249 |
| 5,531,720 A | 7/1996 | Atkins | | |
| 5,810,780 A * | 9/1998 | Brimhall | ........... | A61M 39/0606 604/272 |
| 5,848,996 A * | 12/1998 | Eldor | ................ | A61B 17/3401 604/164.11 |
| 6,280,424 B1 * | 8/2001 | Chang | ............... | A61M 25/0606 604/272 |
| 8,439,877 B2 * | 5/2013 | Burkholz | .............. | A61M 5/329 604/110 |
| 8,956,327 B2 * | 2/2015 | Bierman | ........... | A61M 25/0662 604/164.1 |
| 9,393,382 B2 | 7/2016 | Heck | | |
| 9,399,116 B2 | 7/2016 | Goral et al. | | |
| 2005/0015071 A1 * | 1/2005 | Brimhall | ........... | A61M 25/0693 604/164.01 |
| 2008/0097330 A1 * | 4/2008 | King | ................. | A61M 25/0618 604/164.02 |
| 2008/0147010 A1 * | 6/2008 | Nakajima | ............. | A61M 25/06 604/164.08 |
| 2008/0262430 A1 * | 10/2008 | Anderson | ............ | A61M 25/09 604/165.01 |
| 2008/0294111 A1 * | 11/2008 | Tal | .................... | A61M 25/0606 604/165.01 |
| 2016/0175563 A1 * | 6/2016 | Woehr | .............. | A61M 25/0693 604/168.01 |
| 2016/0235949 A1 * | 8/2016 | Baid | ................... | A61M 5/3291 |
| 2016/0310704 A1 * | 10/2016 | Ng | .................... | A61M 25/0009 |
| 2017/0120010 A1 * | 5/2017 | Burkholz | ............ | A61M 5/1626 |
| 2017/0333642 A1 * | 11/2017 | Shevgoor | ............ | A61M 5/348 |
| 2019/0038876 A1 * | 2/2019 | Isaacson | ............. | A61M 25/065 |
| 2020/0108230 A1 * | 4/2020 | Isaacson | ........... | A61M 25/0618 |

* cited by examiner

CATHETER WITH THREADING FLASH CONFIRMATION

CROSS-REFERENCE TO RELATED APPLICATIONS

The present application claims priority to U.S. Provisional Patent Application No. 62/575,045, filed on Oct. 20, 2017, which is hereby fully incorporated herein by reference.

TECHNICAL FIELD

The present disclosure relates generally to intravenous catheters, and more particularly intravenous catheter assemblies configured to provide a two-stage visual indication during catheter insertion into a vein of a patient.

BACKGROUND

Intravenous (IV) therapy is a versatile technique used for the administration of medical fluids to and withdrawal of bodily fluids from patients. IV therapy has been used for various purposes such as the maintenance of fluid and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittently or continuously by infusion using a needle or catheter. A common intravenous access device utilized by clinicians is the peripheral IV catheter.

A peripheral IV catheter is made of a soft, flexible plastic or silicone, generally between fourteen to twenty-four gauge in size. In conventional venipuncture procedure, a catheter is inserted into a vein of the patient's hand, foot, or the inner aspect of the arm or any vein in the body that will accept an IV catheter. In order to place the IV catheter into the patient's vein, a sharp introducer needle is used to puncture the skin, tissue, and vein wall to provide a path for placement of the catheter into the vein.

Referring to FIGS. 1A-B, a conventional IV needle assembly 50 configured for insertion of an "over the needle" catheter 52 is depicted. Catheter 52 generally includes a catheter tube 54 having a distal end 56 for insertion into a biological site, a proximal end 58 and a flexible wall defining a lumen extending therebetween. Frequently, the proximal end 58 of the catheter tube 54 is operably coupled to a catheter hub 60. Catheter 52 can be operably coupleable to the needle assembly 50, in part by positioning the catheter 52 coaxially over a needle 62 of the needle assembly. The catheter 52 thus rides with the needle 62 through the skin, tissue and vein wall into the patient's vein. Once the catheter tube 54 has entered into the patient's vein, the catheter 52 can be advanced further into the vein as desired and the needle 62 can be withdrawn from the catheter. The catheter 52 can then be secured into place on the patient, and connected to an IV fluid supply. In some instances, the catheter 52 can include an extension tube 64 having a clamp 66 and a Luer lock connector 68 for connection to an IV fluid supply. Such catheters are often referred to as closed system catheters, as they typically include a septum that seals the needle path after the needle has been withdrawn from the catheter, thereby inhibiting blood or bodily fluid from the patient from escaping from the catheter to the ambient environment.

SUMMARY OF THE DISCLOSURE

Embodiments of the present disclosure address problems associated with catheter insertion. In particular, embodiments of the present disclosure provide direct, two-stage, line-of-sight monitoring for successful placement of both an insertion needle and a catheter assembly of an intravenous catheter assembly into a vein of a patient. Accordingly, intravenous catheter assemblies of the present disclosure enable a clinician to: (1) ensure that the needle has entered into the vein of a patient; and (2) ensure that the catheter is being properly threaded into the vein of the patient, while the catheter is being inserted.

Catheter assemblies of the prior art do not provide a visual indication of proper placement of the catheter while the catheter is being threaded into the vein of a patient. Rather, proper catheter placement is not confirmed until either the needle has been completely removed, or the catheter assembly has been vented, thereby enabling blood from the patient to flow through the catheter into a flash chamber. In either case, such confirmation does not take place until catheter insertion is complete.

Accordingly, with catheter assemblies of the prior art it is possible to receive a first positive visual indication that the needle has entered into the vein of a patient, while the catheter (which is positioned proximal to the sharp distal tip of the needle) has not entered into the patient's vein. In these circumstances, it is possible to thread the catheter into the patient along a path outside of the patient's vein. In other circumstances, the catheter may temporarily enter into the patient's vein, only to be inadvertently retracted out of the patient's vein as the needle is withdrawn. In still other circumstances, the catheter may temporarily enter into the patient's vein, but inadvertently be pushed through the opposite wall of the patient's vein during insertion. In all of these circumstances, it is generally not recognized that the catheter has not been properly placed within the vein of the patient, until the catheter has been fully inserted and the needle has been withdrawn. In such cases, the clinician must attempt the procedure again, thereby causing pain and discomfort to the patient, and extending the length of what is otherwise a relatively quick procedure.

One embodiment of the present disclosure provides an intravenous catheter assembly configured to provide a two-stage visual indication during catheter insertion into a vein of a patient. The intravenous catheter assembly includes an insertion needle and a catheter. The insertion needle can have a sharp distal tip, a proximal end, and a radial wall extending therebetween. The insertion needle can define a fluid conduit extending between an inlet positioned on the sharp distal tip and an outlet positioned on the radial wall. The catheter can be coaxially positioned over the insertion needle, having a distal end, a proximal end, and a flexible wall defining a lumen extending therebetween. The catheter can be initially coaxially positioned over the insertion needle in a first position in which the sharp distal tip of the insertion needle extends beyond the distal end of the catheter. An annular space between the radial wall of the insertion needle and the flexible wall of the catheter can be divided into a first axial chamber and a second axial chamber by a formed region of the flexible wall having a diameter configured to inhibit flow between the first axial chamber and the second axial chamber, wherein the outlet of the fluid conduit is position within the first axial chamber, thereby providing a first visual indication during catheter insertion by enabling blood from the vein of the patient to flow into the first axial chamber. The catheter and insertion needle can be shiftable and/or translate axially relative to one another to a second position during catheter insertion, such that the outlet of the fluid conduit is shifted from the first axial chamber to the second axial chamber, thereby providing a second visual indication during catheter insertion by enabling blood from the vein of the patient to flow into the second axial chamber.

Another embodiment of the present disclosure provides a method of providing a two-stage visual indication during catheter insertion into a vein of a patient. The method includes the steps of: coaxially positioning a catheter over an insertion needle in an initial position in which a sharp distal tip of the insertion needle extends beyond a distal end of the catheter, and an annular space between a radial wall of the insertion needle and a flexible wall of the catheter is divided into a first chamber and a second chamber by a formed region in the flexible wall having a diameter configured to inhibit flow between the first axial chamber and the second axial chamber, the insertion needle defining a fluid conduit extending between an inlet positioned on the sharp distal tip and an outlet positioned on the radial wall, wherein in the initial position, the outlet is positioned within the first axial chamber; inserting the sharp distal tip of the insertion needle into the vein of a patient, thereby providing a first visual indication during catheter insertion by enabling blood from the vein of the patient to flow through the fluid conduit and into the first axial chamber; withdrawing the insertion needle and threading the catheter into the vein of the patient, thereby shifting the outlet of the fluid conduit from the first axial chamber to the second axial chamber, thereby providing a second visual indication during catheter insertion by enabling blood from the vein of the patient to flow through the fluid conduit and into the second axial chamber.

In one embodiment, the insertion needle is a hollow hypodermic needle. In one embodiment the inlet of the fluid conduit is in the distal opening of the hollow hypodermic needle and the outlet is a notch defined by the radial wall of the hollow hypodermic needle. In one embodiment, the insertion needle is a solid member defining a fluid conduit groove positioned on the radial wall. In one embodiment the inlet of the fluid conduit is defined by a distal end of the groove and the outlet is defined by a proximal end of the groove. In one embodiment the distal end of the catheter is formed to inhibit distal flow from the first axial chamber.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1A:
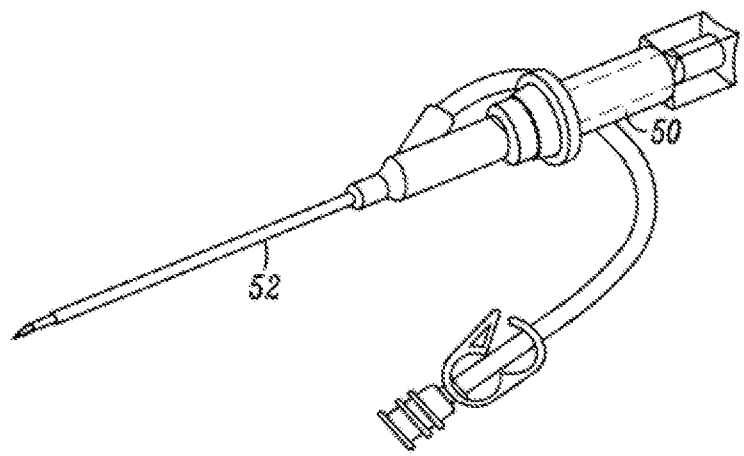
FIG. 1A is a perspective view depicting a conventional IV needle assembly with a catheter positioned over a needle.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1B:
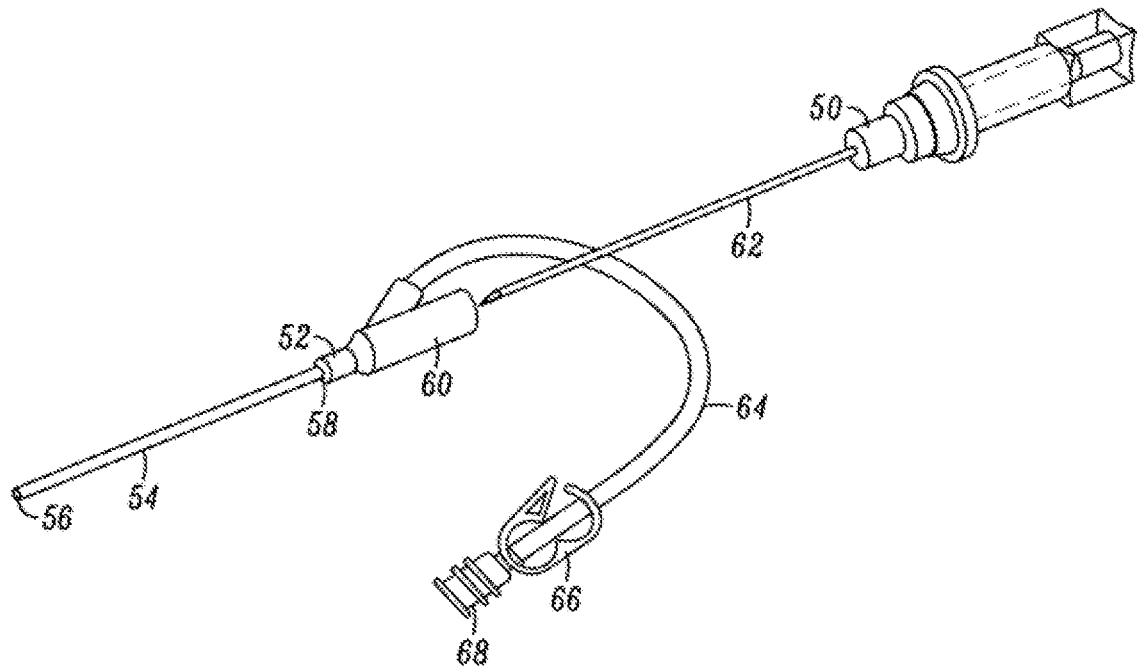
FIG. 1B is a perspective view depicting the conventional IV needle assembly of FIG. 1A with the catheter removed from the needle.

Referring to FIGS. 1A-B, a conventional IV catheter assembly 50 is depicted. Details of the conventional IV catheter assembly 50 are described in the Background section above.

Figure 2:
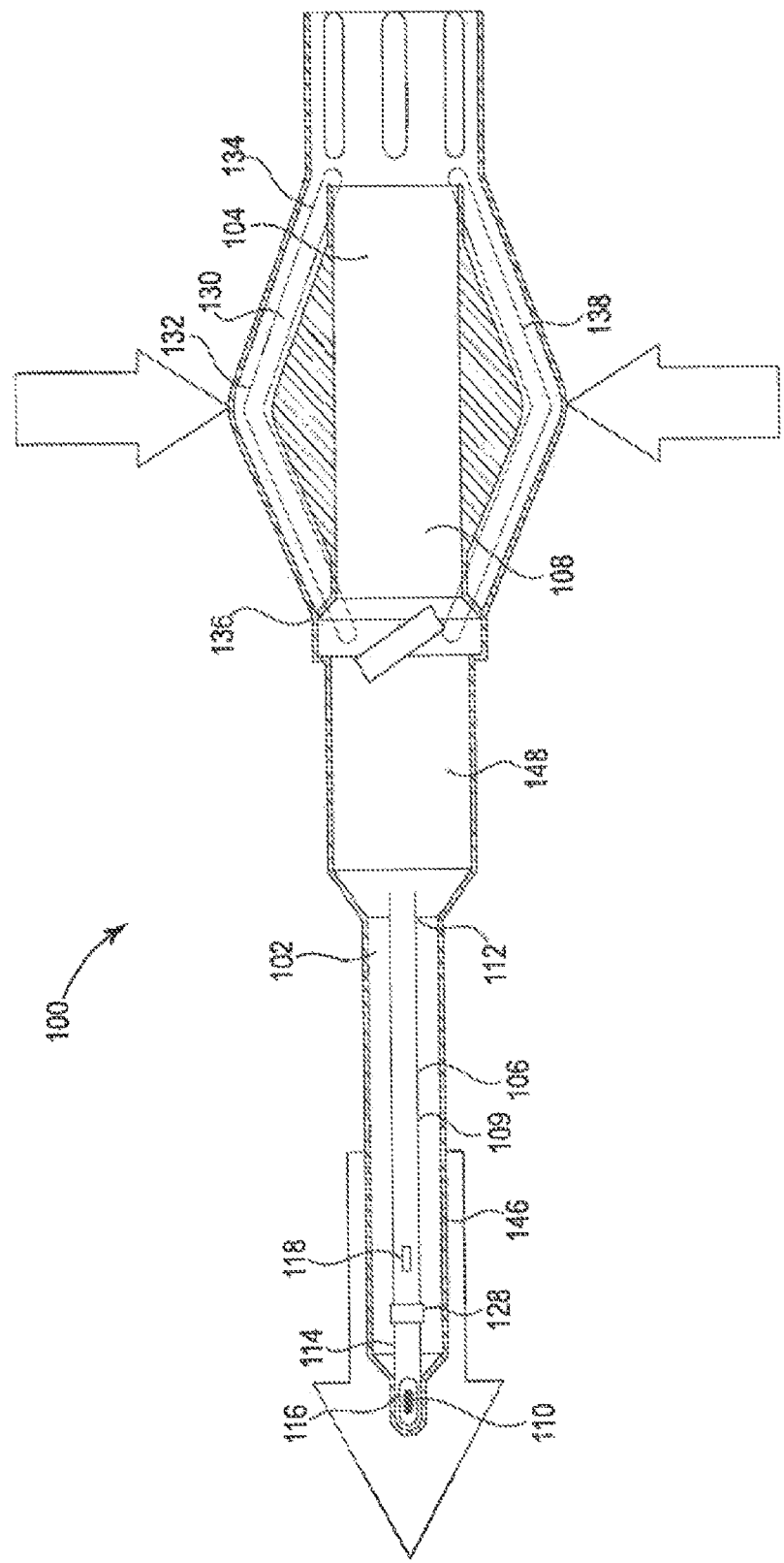
FIG. 2 is a plan view depicting an intravenous catheter assembly in accordance with an embodiment of the disclosure.

Referring to FIG. 2, an intravenous catheter assembly 100 is depicted in accordance with an embodiment of the disclosure. In one embodiment, the intravenous catheter assembly 100 includes a catheter assembly 102 and a catheter insertion device 104. Various types of catheter insertion devices 104 are marketed by Smiths Medical ASD, Inc. of St. Paul, Minn., under the TELCO trademark. One embodiment of the catheter insertion device 104 (such as that depicted in FIGS. 1A-B) is described in U.S. Pat. Nos. 7,291,130 and 8,257,322 (depicting an IV catheter insertion device marketed by Smiths ASD, under the INTUITIV trademark) both of which are incorporated by reference herein.

The catheter insertion device 104 can include an insertion needle 106 operably coupled to a needle hub 108. The insertion needle 106 can include an elongate, cylindrically shaped radial wall 109 defining a lumen that extends between a sharpened distal needle tip 110 and a proximal end 112. The sharp distal tip 110 can be constructed and arranged to pierce the skin of a subject during catheter insertion. For example, in one embodiment, the sharp distal tip 110 can include a V-point designed to reduce the penetration force used to penetrate the needle 106 and a portion of the catheter assembly 102 through the skin, tissue, and vein wall of a subject. In one embodiment, the length of the insertion needle 106 can be extended to aid in the insertion of the catheter assembly 102 into obese patients.

It is to be appreciated that the term "distal," as used herein, refers to the direction along an axis the lies parallel to the insertion needle 106 of the intravenous catheter assembly 100 that is closest to the subject during catheter insertion. Conversely, the term "proximal," as used herein, refers to the direction lying along the axis parallel to the insertion needle 106 that is further away from the subject when the catheter is inserted into the vein of the subject, opposite to the distal direction.

Figures 4A, 4B:
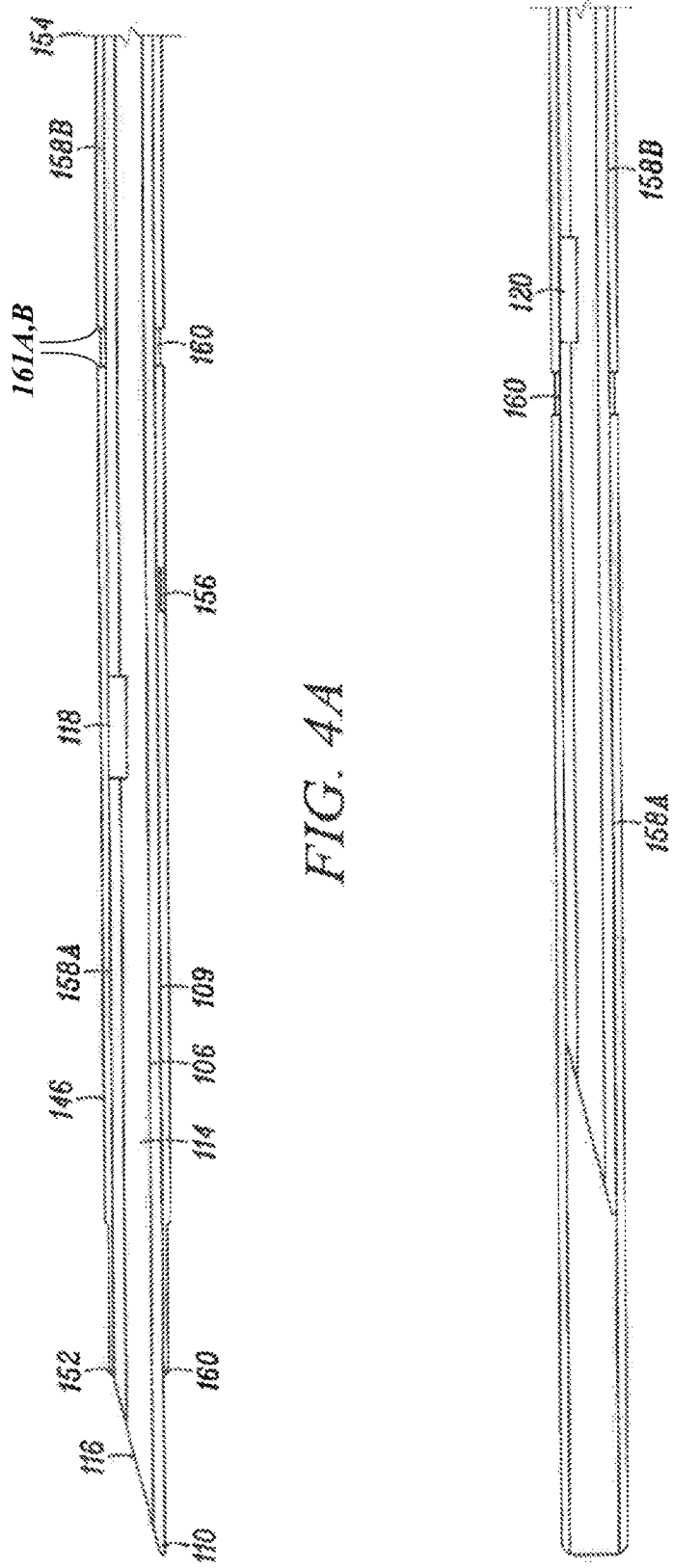
FIG. 4A is a partial, cross-sectional view of a catheter tube coaxially positioned over an insertion needle, in accordance with an embodiment of the disclosure.
FIG. 4B is a partial, cross-sectional view of the catheter tube and insertion needle of FIG. 4A, in which the catheter tube and insertion needle have been shifted relative to one another.
Figure 5A:
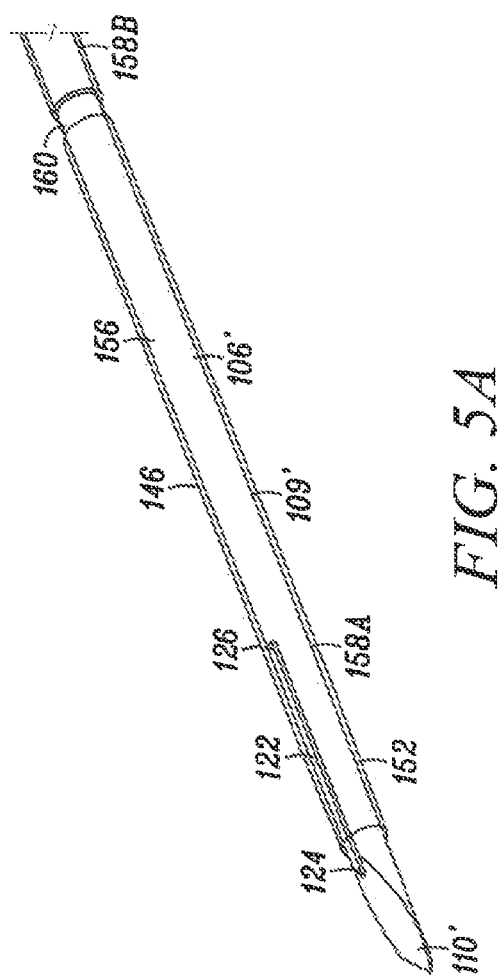
FIG. 5A is a partial, cross-sectional view of a catheter tube coaxially positioned over an insertion needle, in accordance with an alternative embodiment of the disclosure.
Figure 5B:
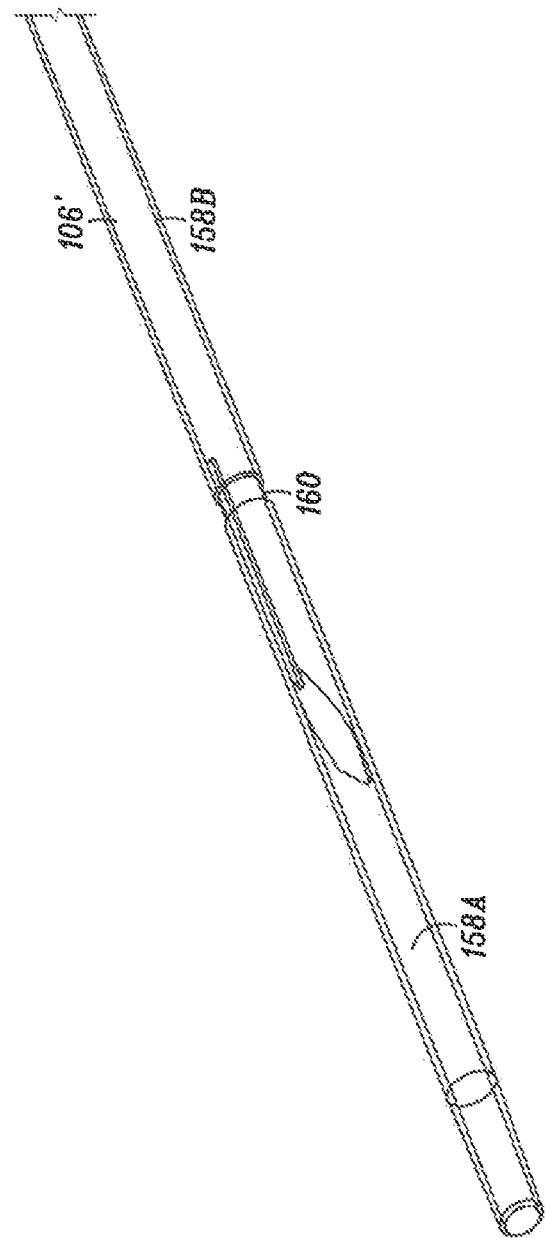
FIG. 5B is a partial, cross-sectional view of the catheter tube and insertion needle of FIG. 5A, in which the catheter tube and insertion needle have been shifted relative to one another.

In one embodiment, the needle 106 can define a fluid conduit 114 extending between an inlet 116 positioned on the sharp distal tip 110 and an outlet 118 positioned on the radial wall 109. In this embodiment, blood or bodily fluid can enter the fluid conduit 114 through the inlet 116 when the sharp distal tip 110 enters the vein. As blood flows proximally in the fluid conduit 114, some of the blood passes through the outlet 118. As depicted in FIGS. 4A-B, in one embodiment, the insertion needle 106 can be a hollow hypodermic needle, wherein the inlet 116 of the fluid conduit 114 is in the distal opening of the hollow hypodermic needle, and the outlet 118 is a notch defined by the radial wall 109 of the hollow hypodermic needle. Alternatively, as depicted in FIGS. 5A-B, in one embodiment, the insertion needle 106 is a solid member defining a groove 122 positioned on the radial wall 109 representing the fluid conduit 114, wherein the inlet 116 of the fluid conduit is defined by a distal end of the groove 122, and the outlet 118 is defined by a proximal end 126 of the groove 122.

In some embodiments, the insertion needle 106 can further include a transition 128 that has a different cross-sectional size and/or shape then portions of the needle 106 positioned proximal to the transition 128. The transition 128 (alternatively referred to as a needle bump or cannula bump) can be created by crimping opposed sides of the needle 106, or otherwise disrupting the structure of the needle 106, so that the outer surfaces of the needle 106 extend to a larger radial position than other portions of the needle 106, as measured from the center of the needle axis. Transitions 128 can be formed differently, according to alternate embodiments, such as by adding material to the exterior of the needle, among other ways.

The proximal end 112 of the needle 106 can be operably coupled to the needle hub 108. The needle hub 108 can be operably coupled to a needle grip 130. In one embodiment, the needle grip 130 can be a flexible member including one or more living hinges 132. The needle grip 130 can be fixedly coupled to the needle hub 108 at a proximal portion 134, and can be translationally coupled to the needle hub 108 at a distal portion 136. In one embodiment, portions of the needle grip 130 can be urged or brought together by the application of an external force thereby straightening a bend 138 formed in the needle grip 130, thereby causing the distal portion 136 to shift distally relative to the needle hub 108. In one embodiment, the distal shifting of the distal portion 136 can cause the catheter assembly 102 to shift distally relative to the catheter insertion device 104. For example, in one embodiment, squeezing of the needle grip 130 can cause the catheter to distally advance 2-3 mm.

Figure 3:
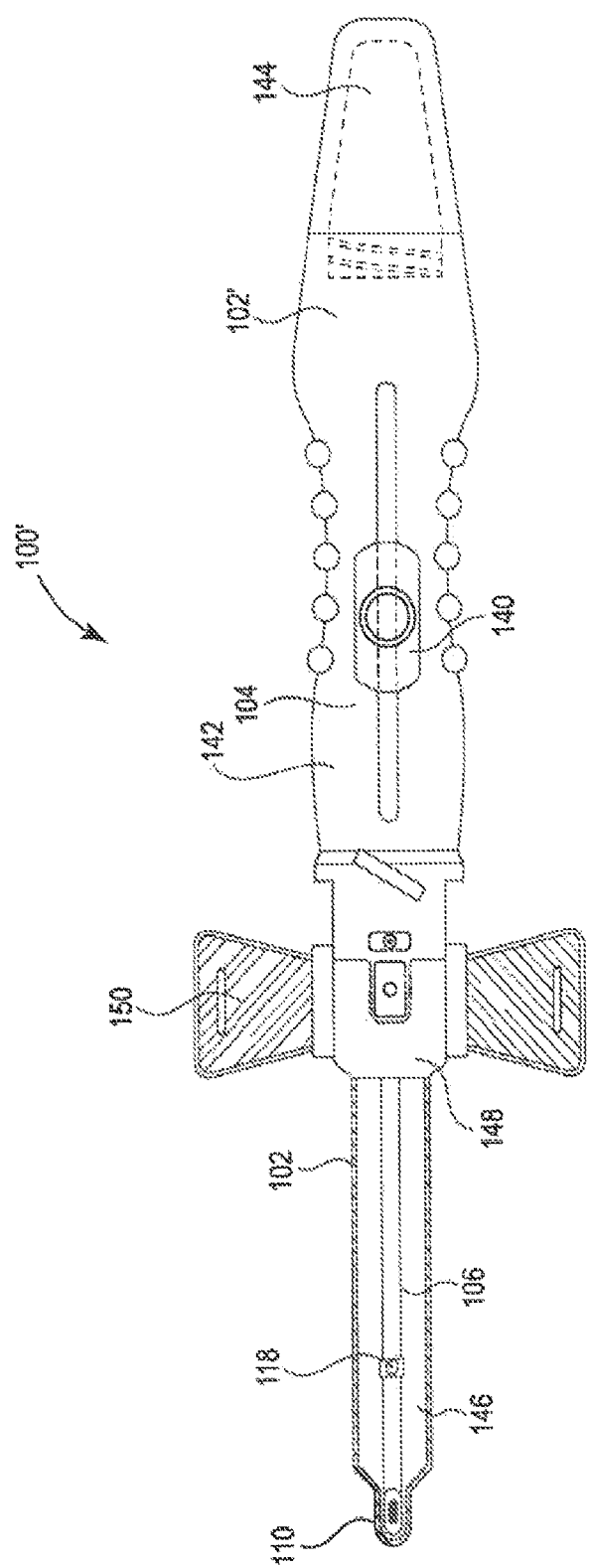
FIG. 3 is a plan view depicting an intravenous catheter assembly in accordance with an alternative embodiment of the disclosure.

Referring to FIG. 3, in one embodiment, the catheter insertion device 102' can provide a safety needle assembly, which functions to house the sharpened distal tip 110 of the insertion needle 106 to reduce the likelihood of an inadvertent needlestick. FIG. 3 depicts the catheter insertion device 104 in a first, or ready for use position, in which the catheter assembly 102 is selectively coupled to the catheter insertion device 104, with the sharp distal tip 110 of the insertion needle 106 protruding from a distal end of the catheter assembly 102.

To insert the catheter assembly 102 into a vein of a patient or subject, a clinician first removes the intravenous catheter assembly 100' from its packaging. In some cases, a needle sheath is removed to expose the sharp distal tip 110 of the insertion needle 106. The clinician then punctures an identified site of the subject with the sharp distal tip 110 and urges and/or advances the needle 106 distally until the sharp distal tip 110 enters the vein of the subject. The catheter assembly 102 can then be moved distally over the needle by advancing an internal mechanism affixed to the needle assembly 140, threading the catheter assembly 102 into the vein of the subject as the needle 106 is held stationary. With the catheter assembly 102 positioned as desired, the clinician can withdraw the needle 106 by continuing to advance the needle assembly 140 distally while holding the catheter assembly 102 generally stationary with respect to the subject. The needle assembly 140 can be advanced distally until the insertion needle 106 of the catheter insertion device 104 is separated from the catheter assembly 102 and safely housed within a needle housing 142 of the catheter insertion device 104. In one embodiment, the catheter insertion device 104 can further include a removable blood sample collection vial 144, configured to collect a sample of blood flowing through the lumen of the insertion needle 106.

The catheter assembly 102 generally includes a catheter tube 146 and a catheter hub 148. As depicted in FIG. 3, in one embodiment, the catheter assembly 102 can optionally include a wing assembly 150. Further, in some embodiments, the catheter assembly 102 can include an extension tube, an extension tube clamp, a needleless connector, and a vent cap. Accordingly, the catheter assembly 102 can be a closed system catheter configured to inhibit blood from escaping after withdrawal of the needle 106.

With additional reference to FIGS. 4A-B, a partial, cross-sectional view of an insertion needle 106 and catheter tube 146 is depicted in accordance with an embodiment of the disclosure. As depicted, the catheter tube 146 is coaxially positioned over the insertion needle 106. The catheter has a distal end 152, a proximal end 154 and a flexible wall 156 defining a lumen extending therebetween. As depicted in FIG. 4A, the catheter tube 146 is initially coaxially positioned over the insertion needle 106 in a first position, in which the sharp distal tip 110 extends beyond the distal end 152 of the catheter tube 146. An annular space 158A/B is defined between the radial wall 109 of the insertion needle 106 and the flexible wall 156 of the catheter tube 146. In one embodiment, the annular space 158 is divided into a first axial chamber 158A and a second axial chamber 158B by a formed region 160 of the flexible wall 156, wherein the formed region 160 has an internal diameter sized to approximate the outer diameter of the insertion needle 106, such that flow of blood or bodily fluid between the first axial chamber 158A and the second axial chamber 158B along the annular space 158 is inhibited. As illustrated, formed region 160 can have a flat portion connected to a pair of non-tapered walls 161A,B, all defined circumferentially into the flexible wall 156. In the initial position, the outlet 118 of the fluid conduit 114 is positioned within the first axial chamber 158A, thereby providing a first visual indication during catheter insertion, by enabling blood from the vein of the patient to flow into the first axial chamber 158A.

In one embodiment, the distal end 152 of the catheter tube 146 additionally includes a formed region 160 having an internal diameter sized to approximate the outer diameter of the insertion needle 106. In some embodiments, the formed region 160 serves to minimize the diameter of the catheter tube 146 for ease of insertion of the catheter assembly 102 into the tissue of a patient.

As depicted in FIG. 4B, the catheter tube 146 and insertion needle 106 can translate axially relative to one another to a second position during catheter insertion, such that the outlet 118 of the fluid conduit 114 is shifted from the first axial chamber 158A to the second axial chamber 158B, thereby providing a second visual indication during catheter insertion by enabling blood from the vein of the patient to flow into the second axial chamber 158B.

Referring to FIGS. 5A-B, a partial, cross-sectional view of an insertion needle 106' and catheter tube 146 is depicted in accordance with another embodiment of the disclosure. As depicted in FIG. 5A, the catheter tube 146 is initially coaxially positioned over the insertion needle 106' in a first position, in which the sharp distal tip 110' extends beyond the distal end 152 of the catheter tube 146. An annular space 158A/B is defined between the radial wall 109' of the insertion needle 106' and the flexible wall 156 of the catheter tube 146. In one embodiment, the annular space 158A/B is divided into a first axial chamber 158A and a second axial chamber 158B by a formed region 160 of the flexible wall 156, wherein the formed region 160 has an internal diameter sized to approximate the outer diameter of the insertion needle 106', such that flow of blood or bodily fluid between the first axial chamber 158A and the second axial chamber 158B along the annular space 158A/B is inhibited. In the initial position, the outlet 118 of the groove 122 is positioned within the first axial chamber 158A, thereby providing a first visual indication during catheter insertion, by enabling blood from the vein of the patient to flow into the first axial chamber 158A.

As depicted in FIG. 5B, the catheter tube 146 and insertion needle 106' translate axially relative to one another to a second position during catheter insertion, such that the outlet 118 of the groove 122 is shifted from the first axial chamber 158A to the second axial chamber 158B, thereby providing a second visual indication during catheter insertion by enabling blood from the vein of the patient to flow into the second axial chamber 158B.

Figure 6A:
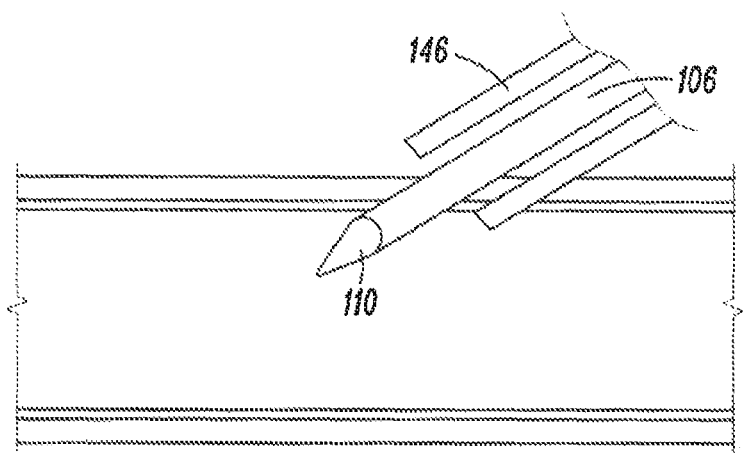
FIG. 6A depicts the insertion of an insertion catheter assembly into a vein of a patient, in accordance with an embodiment of the disclosure.
Figure 6B:
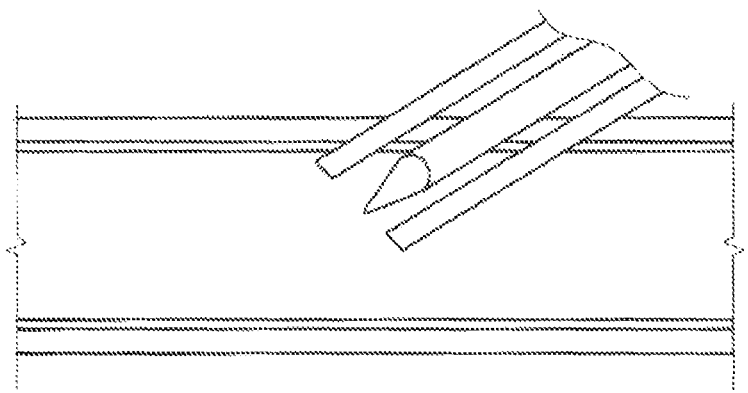
FIG. 6B depicts an advancement of a catheter tube over an insertion needle, in accordance with an embodiment of the disclosure.
Figure 6C:
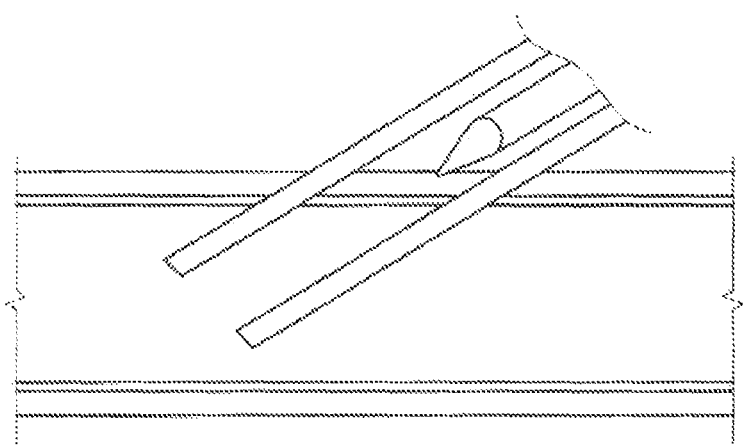
FIG. 6C depicts a threading of a catheter tube into a vein of a patient, in accordance with an embodiment of the disclosure.

With additional references to FIGS. 6A-C, insertion of the intravenous catheter assembly 100 into the vein of a patient, advancement of the catheter tube 146 over the insertion needle 106, and threading of the catheter tube into the vein of the patient are depicted in accordance with an embodiment of the disclosure. Initially the catheter tube 146 is coaxially positioned over the insertion needle 106 in an initial position, in which the sharp distal tip 110 of the insertion needle 106 extends beyond a distal end 152 of the catheter. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy-five mm distal to the site.

As depicted in FIG. 6A, the sharp distal tip 110 of the needle 106 is introduced into the vein by inserting the bevel of the sharp distal tip 110 into the vein at about a twenty to thirty-degree angle with the bevel facing up in order to pierce one wall of the vein. In some embodiments, during this process the clinician grips the catheter insertion device 104 for optimum control. If successful, blood will flow through the fluid conduit 114 and into the first axial chamber 158A, thereby providing a positive indication that the sharp distal tip 110 of the needle 106 is positioned within the vein of a patient.

As depicted in FIG. 6B, to finish placement, the intravenous catheter assembly 100 is lowered towards the skin to decrease the entry angle. The clinician then begins to advance the catheter assembly 102 over the insertion needle 106. Once the catheter assembly 102 has been advanced, the clinician may withdraw the insertion needle 106. In some cases, the advance of the catheter assembly 102 and the withdrawal of the insertion needle 106 occur simultaneously.

As depicted in FIG. 6C, once the outlet 118 of the fluid conduit 114 shifts from the first axial chamber 158A to the second axial chamber 158B, blood flows through the fluid conduit 114 and into the second axial chamber 158B, thereby providing a positive indication that the catheter tube 146 is positioned within the vein of a patient. Accordingly, embodiments of the present disclosure provide a two-stage flash to first serve as an aid in ensuring that the needle 106 has entered into the vein of the patient, and second to serve as an aid to ensure that the catheter tube 146 is being properly threaded into the vein of the patient, while the catheter tube 146 is being inserted.

The clinician can then secure the catheter assembly 102 in place by securing the catheter hub 148 and/or wing assembly 150 to the biological site by gauze and adhesive tape. The catheter assembly 102 can then be connected to an IV fluid supply configured to supply medicament to the patient, or withdraw fluid from the patient.

Figure 7A:
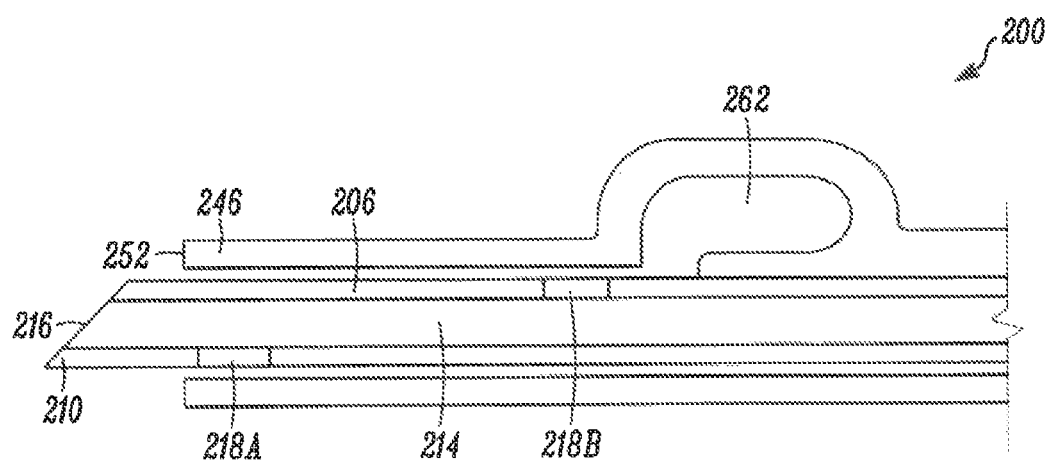
FIG. 7A is a partial, cross-sectional view of a catheter tube coaxially positioned over an insertion needle in accordance with an alternative embodiment of the disclosure.
Figure 7B:
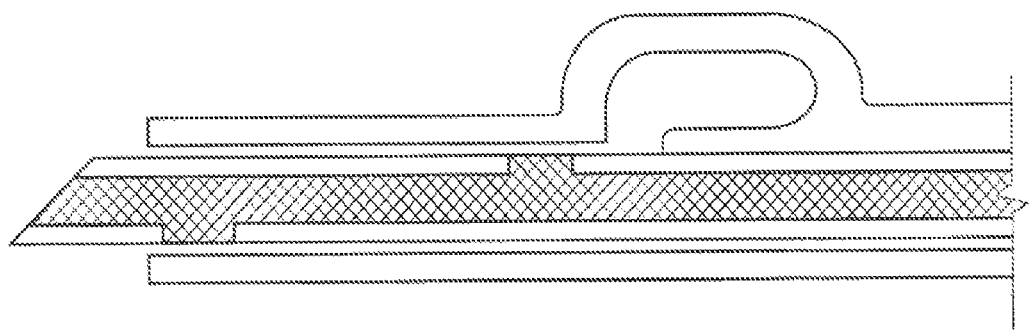
FIG. 7B depicts an insertion of the insertion needle and catheter tube of FIG. 7A into a vein of a patient.
Figure 7C:
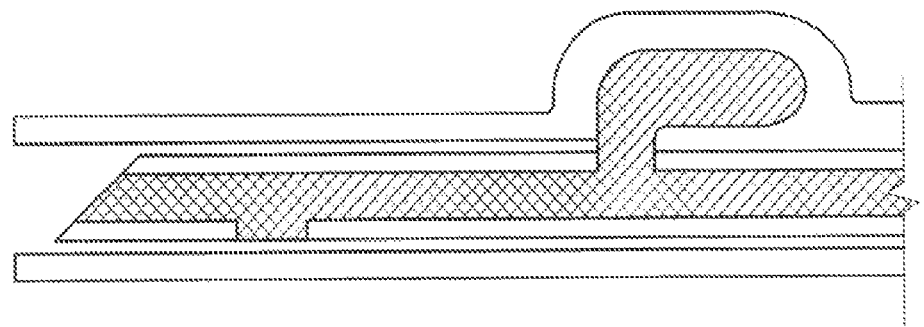
FIG. 7C depicts a threading of the catheter tube of FIG. 7B into a vein of a patient.

Referring to FIGS. 7A-C, an alternative embodiment of an intravenous catheter assembly 200 is depicted. In this embodiment, the insertion needle 206 can define a fluid conduit 214 including an inlet 216, a first outlet 218A, and a second outlet 218B. As depicted in FIG. 7A, initially the catheter tube 246 is coaxially positioned over the insertion needle 206 in an initial position, in which the sharp distal tip 210 of the insertion needle 206 extends beyond a distal end 252 of the catheter. As illustrated in FIGS. 7A-7C, the first outlet 218A can be circumferentially offset from the second outlet along a circumference of the insertion needle 206, such that a first visual indication by the first outlet 218A is diametrically separated from the second visual indication by the second outlet 218B along the insertion needle 206 circumference.

As depicted in FIG. 7B, when the sharp distal tip 210 of the needle 206 is introduced into the vein, blood flows through the fluid conduit 214 to the respective first and second outlets 218A/B. In some embodiments, the catheter tube 246 can be constructed of a transparent or translucent material, such that a clinician can observe blood present at the first outlet 218A, thereby providing a positive indication that the sharp distal tip 210 of the needle 216 is positioned within the vein of a patient.

In some embodiments, the catheter tube 246 can include a secondary confirmation chamber 262. For example, in one embodiment, the secondary confirmation chamber 262 can form a cavity or annular space into which blood from the patient can flow. As illustrated in FIGS. 7A-7C, the secondary confirmation chamber 262 may extend outward from the flexible wall of the catheter tube 246 and can define an opening to receive blood into an enclosed cavity. As further illustrated in FIGS. 7A-7C, the secondary confirmation chamber 262 can have a substantially L-shaped cross-section defined by the opening and the enclosed cavity. As depicted in FIG. 7C, once the second outlet 218B shifts from the initial position into fluid communication with the secondary confirmation chamber, blood flows through the conduit 214 and into the secondary confirmation chamber 262 thereby providing a positive indication that the catheter tube 246 is positioned within the vein of a patient. Accordingly, embodiments of the present disclosure provide a two-stage flash to first serve as an aid in ensuring that the needle 206 has entered into the vein of the patient, and second to serve as an aid to ensure that the catheter tube 246 is being properly threaded into the vein of the patient while the catheter tube 246 is being inserted.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various example intravenous catheter assembly embodiments are described herein for use in accessing the vein of the subject. It is to be appreciated, however, that the example embodiments described herein can alternatively be used to access the vasculature of a subject in locations other than the vein, including but not limited to the artery of the subject. It is additionally to be appreciated that the term "clinician" refers to any individual that can perform a catheter insertion procedure with any of the example embodiments described herein or combinations thereof. Similarly, the term "subject," as used herein, is to be understood to refer to an individual or object in which a catheter is to be inserted, whether human, animal, or inanimate. Various descriptions are made herein, for the sake of convenience, with respect to procedures being performed by a clinician to access the vein of the subject, while the disclosure is not limited in this respect.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An intravenous catheter assembly configured to provide a two-stage visual indication during catheter insertion into a vein of a patient, the intravenous catheter assembly comprising:

an insertion needle having a sharp distal tip, a proximal end, and a radial wall extending therebetween, the insertion needle defining a fluid conduit extending between an inlet positioned on the sharp distal tip and a first outlet and a second outlet positioned on the radial wall, the insertion needle defining a central needle axis between the inlet and the first and second outlets; and a catheter coaxially positionable over the insertion needle and having a distal end, a proximal end, and a flexible wall defining a lumen extending therebetween, the catheter coaxially positionable over the insertion needle in a first position in which the sharp distal tip of the insertion needle extends beyond the distal end of the catheter, an annular space being presented between the radial wall of the insertion needle and the flexible wall of the catheter, the annular space being coupled to a secondary confirmation chamber extending outward from the flexible wall of the catheter, the secondary confirmation chamber configured to inhibit blood flow through the insertion needle, wherein the secondary confirmation chamber defines an opening to receive blood into an enclosed cavity, the secondary confirmation chamber having a substantially L-shaped cross-section defined by the opening and the enclosed cavity, the first outlet being positioned on the radial wall within the annular space when the catheter is in the first position thereby providing a first visual indication during catheter insertion by enabling blood from the vein of the patient to flow through the first outlet clear of obstruction yet retained in generally fluid tight relationship within the annular space, the catheter and the insertion needle translatable axially relative to one another to a second position during catheter insertion, such that the second outlet positioned on the radial wall is shifted to the secondary confirmation chamber, thereby providing a second visual indication during catheter insertion by enabling blood from the vein of the patient to flow through the opening of the secondary confirmation chamber and into the enclosed cavity for visual observation, wherein the first outlet is circumferentially offset from the second outlet along a circumference of the insertion needle, such that the first visual indication by the first outlet is diametrically separated from the second visual indication by the second outlet.

2. The intravenous catheter assembly of claim 1, wherein the insertion needle is a hollow hypodermic needle.

\* \* \* \* \*